United States Patent [19]

Skrumsager et al.

[11] Patent Number: 5,756,539
[45] Date of Patent: May 26, 1998

[54] 3, 4-DIPHENYL CHROMANS FOR INHIBITING ONE OR MORE PSYCHIATRIC DISORDERS

[75] Inventors: Birte Kloppenborg Skrumsager, Brønshøj; Erik Bardrum Nielsen, Værløse; Birgitte Hjort Guldhammer, Hillerød, all of Denmark

[73] Assignee: Novo Nordis A/S, Bagsvaerd, Denmark

[21] Appl. No.: 803,483

[22] Filed: Feb. 20, 1997

Related U.S. Application Data

[63] Continuation-in-part of Ser. No. 781,567, Jan. 9, 1997, which is a continuation-in-part of Ser. No. 678,261, Jul. 11, 1996.

[60] Provisional application No. 60/031,245, Nov. 12, 1996.

[30] Foreign Application Priority Data

Jan. 29, 1997 [DK] Denmark .................... 0110/97

[51] Int. Cl.⁶ .................... A61K 31/35; A61K 31/41
[52] U.S. Cl. .................... 514/456; 514/422
[58] Field of Search .................... 514/456, 422

[56] References Cited

U.S. PATENT DOCUMENTS

| | | | |
|---|---|---|---|
| 3,340,276 | 9/1967 | Carney et al. | 260/345.2 |
| 3,822,287 | 7/1974 | Bolger | 260/326.5 D |
| 4,447,622 | 5/1984 | Salman et al. | 548/525 |
| 5,280,040 | 1/1994 | Labroo et al. | 514/422 |
| 5,453,442 | 9/1995 | Bryant et al. | 514/408 |

FOREIGN PATENT DOCUMENTS

WO 96/22091  7/1996  WIPO .

OTHER PUBLICATIONS

Ray, S. et al., Jour. of Med. Chem., vol. 19, No. 2, pp. 276–279 (1976).
Abstract—Jour. of Bone and Mineral Res., vol. 9, Supple. 1, p. S394, 1994.
Sankaran, M.S. et al., Contraception, vol. 9, No. 3, pp. 279–289, 1974.
Grubb, G.S., Obstetrics and Gynecology, vol. 3, pp. 491–495, 1991.
Singh, M.M. et al., Acta. Endocrinologica, vol. 126, pp. 444–450, 1992.
Ray et al., IN 129187, Council of Scientific & Industrial Research (Government of India) Aug., 1975.
Mortola, J.F., Current Opinion in Endocrinology and Diabetes, vol. 2, pp. 483–492 (1995).
Chak, I.M. et al., Indian Jour. of Exper. Biol., vol. 15, pp. 1159–1161 1977).
Nemeroff, C. B., Neuropsychopharmacology, vol. 6, No. 2, pp. 69–75 (1992).
Nerozzi, D., et al., J. Endocrinol. Invest. vol. 11, pp. 697–701, (1988).
Glowa, J.R., et al., Prog. Neuro–Psychopharmacol. & Biol. Psychiat., vol. 15, pp. 379–391 (1991).
Grino, M. et al., Endocrine, vol. 3, pp. 395–398, (1995).
Fink et al., Cellular and Molecular Neurobiology, vol. 16, pp. 337–344 (1996).
Bartus, R.T. et al., Science, vol. 217, pp. 408–417 (1982).
Gould, E. et al., The Journal of Neuroscience, vol. 10, pp. 1286–1291 (1990).
Kampen, D.L. et al., Obstetrics & Gynecology, vol. 83, No. 6, pp. 979–983 (1994).
Phillips, S.M. et al., Psychoneuroendocrinology, vol. 17, No. 5, pp. 485–495 (1992).

Primary Examiner—Phyllis G. Spivack
Attorney, Agent, or Firm—Steve T. Zelson; Cheryl H. Agris

[57] ABSTRACT

A method of inhibiting one or more psychiatric disorders is disclosed comprising administering a compound of formula I

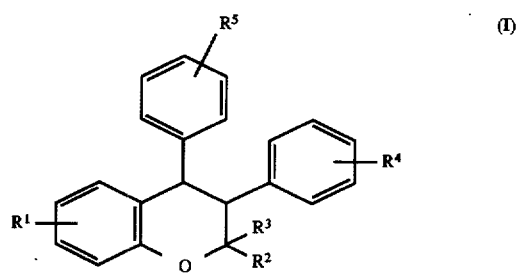

(I)

wherein $R^1$, $R^4$ and $R^5$ are individually hydrogen, hydroxy, halogen, trifluoromethyl, $C_{1-6}$ alkyl, $C_{1-6}$ alkoxy or (tertiary amino)$C_{1-6}$ alkoxy; and $R^2$ and $R^3$ are individually hydrogen or $C_{1-6}$ alkyl, or a pharmaceutically acceptable salt thereof.

19 Claims, No Drawings

5,756,539

3,4-DIPHENYL CHROMANS FOR INHIBITING ONE OR MORE PSYCHIATRIC DISORDERS

CROSS-REFERENCE TO RELATED APPLICATIONS

This application is a continuation-in-part of application Ser. no. 08/781,567 filed on Jan. 9, 1997, which is a continuation-in-part of application Ser. No. 08/678,261 filed Jul. 11, 1996 and claims priority under 35 U.S.C. 119 of U.S. provisional applications Ser. Nos. 60/009,834 filed on Jan. 11, 1996 and 60/031,245 filed on Nov. 12, 1996 and Danish application serial no. 110/97 filed Jan. 29, 1997, the contents of which are fully incorporated herein by reference.

FIELD OF THIS INVENTEDN

The present invention relates to the use of compounds of the general formula I for inhibiting one or more psychiatric disorders. The present invention also embraces pharmaceutical compositions comprising these compounds and methods of using the compounds and their pharmaceutical compositions.

BACKGROUND OF THIS INVENTION

Psychiatric disorders are those disorders known to be included in the definition by those skilled in the art, which includes e.g. anxiety, depression, tension, irritability, memory loss, mood swings, motivational defects, cognitive disorders, attention deficits, schizophrenia, psychoses, winter depressions.

Extensive research has been conducted for a number of years directed toward the development of compounds capable of treating anxiety in humans that are safer to the user and which exhibit fewer side effects. For example, several clinically established anxiolytic agents such as the barbiturates, meprobamate and the benzodiazepines have numerous side effects such as potential for abuse and addiction or potentiation of the effects of alcohol. The mechanism of action of these compounds is believed to involve the GABA/benzodiazepine receptor complex in humans.

It has been observed that during the course of life, women can suffer from mood swings according to their biological hormonal rhythms. Examples include premenstrual psychological instability of mood as well as the instability of mood often observed during the menopause. However, the natural rhytmicity of hormonal production in women may also be affected by environmental conditions, for example, stress induced suppression of estrogen production. Until now, mainly antidepressants and benzodiazepines have been used to treat these symptoms. Thus, there exists a need for a compound which inhibit mood swings and thus causes a greater degree of physical comfort by enhancing or stabilizing mood.

Corticotropin-releasing factor (CRF) levels have been associated with depression, anxiety and sleeplessness (Nemeroff, *Neuropsychopharmacology* (1992) 6, 69–75, Nerozzi et al., *J. Endocrinol, Invest.* (1988) 11, 697–701 and Glowa et al., *Prog. Neuropsychopharmacol Biol. Psychiatry* (1991) 15, 379–391). It is known that estrogens can regulate negatively CRF expression in the brain (Grino et al., *Encocrine* (1995) 3, 395–398) Thus, this may provide a mechanism by which low levels of estrogens may lead to enhanced CRF tonus which again in turn may mediate depression, anxiety and sleeplessness.

Furthermore, it has recently been found that estradol increases the density of 5-HT$_{2A}$ receptors in cerbral cortex and nucleus accumbens. This may provide an additional mechanism by which estrogen therapy is effective in reducing significantly the symptoms in women with major depressive disorder (Fink et al., *Cellular and Molecular Neurobiology* (1996) 16, 325–344) as low levels ao 5-HT activity in the brain is associated with depression (e.g. 5-HT uptake inhibitors which increase 5-HT tonus are effective antidepressants).

Advances in neuroscience during the past decade have provided a rationale for the ways in which estrogen may affect cognitive functions in women. First, it has been known for some time that the hippocampus, a brain structure that is critically important in learning and memory, contains estrogen receptors (Pfaff D. W.: *Estrogen and brain function*, New York, Springer-Verlag 1980). There are several ways in which estrogen may affect the brain to enhance or preserve cognitive functions. First, estrogen increases choline acetyltransferase, the enzyme needed to synthezise acetylcholine, a neurotransmitter thought to be critical for memory and learning (Bartus et al. *The cholinergic hypothesis of memory dysfunction in Science* 217 (1982), 208–417). Secondly, evidence from animal studies has shown that estrogen can enhance synpatogenesis in an area of the brain also known to be important for memory (Gould et al.: Gonadal steroids regulate dendritic spine density in hippocampal pyramidal cells in adulthood in J. Neurosci. 10 (1990), 1286–91).

Findings have shown improvements of concentration and memory in healthy middle-aged and older postmenopausal women in response to estradiol, estriol succinate, estrone or norethisterone. Improvement was observed in healthy, well-functioning postmenopausal women in treatment with various estrogens (Kampen and Sherwin, Obstet. Gynecol (1994), 83, 979–83). Improvement was observed in women with an average age of 48 years (Philips and Sherwin. Psychoneuroendocrinology (1992), 17, 485–95). However, it is well known that estrogen treatment can cause various unwanted effects such as stimulation of the endomnetrium. Thus, there is a need for a new compound, which can be used for delaying or preventing loss of cognitive function or enhancing the cognitive function, but which is safe and causes less side effects than known compounds.

Centchroman is a non-steroidal compound known to have antiestrogenic activity. It is in use in India as an oral contraceptive (see, for example, Salman et al., U.S. Pat. No. 4,447,622; Singh et al., *Acta Endocrinal (Copenh)* 126 (1992), 444–450; Grubb, *Curr Opin Obstet Gynecol* 3 (1991), 491–495; Sankaran et al., *Contraception* 9 (1974), 279–289; Indian Patent Specification No. 129187). Centchroman has also been investigated as an anti-cancer agent for treatment of advanced breast cancer (Misra et al., *Int J Cancer* 43 (1989), 781–783. Recently, centchroman as a racemate has been found as a potent cholesterol lowering pharmaceutical expressed by a significant decrease of the serum concentrations (S. D. Bain et al., *J Min Bon Res* (1994), S 394).

U.S. Pat. No. 5,453,442 describes methods of lowering serum cholesterol and inhibiting smoother muscle cell proliferation in humans and inhibiting uterine fibroid disease and endometriosis in women by administering compounds of formula I as shown therein. Furthermore, U.S. Pat. No. 5,280,040 describes methods and pharmaceutical compositions for reducing bone loss using 3,4-diaryl chromans and their pharmaceutically acceptable salts. There is no disclosure in the patents of using the compounds to treat or prevent one or more psychiatric disorders.

One object of the present invention is to provide compounds which can effectively be used in the treatment or prophylaxis of one or more psychiatric disorders and which is safe and causes less side effects.

DETAILED DESCRIPTION OF THIS INVENTION

This invention provides the use of compounds of the general formula I

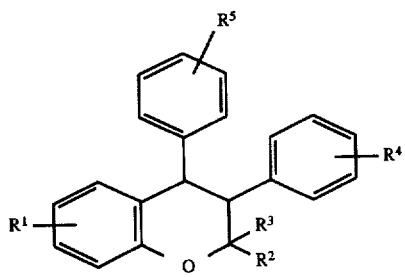

wherein $R^1$, $R^4$ and $R^5$ are individually hydrogen, hydroxy, halogen, trifluoromethyl, $C_{1-6}$ alkyl, $C_{1-6}$ alkoxy or (tertiary amino)($C_{1-6}$ alkoxy); and $R^2$ and $R^3$ are individually hydrogen or $C_{1-6}$ alkyl, or as a pharmaceutically acceptable salt for the manufacture of a pharmaceutical composition for inhibiting one or more psychiatric disorders.

Thus the compounds of above general formula I can be used in methods for inhibiting of mood swings. The compounds have a specific mood stabilizing effect not only counteracting the fluctations in mood during the pre menstrual period or the menopause, but also for example due to stressfull situations. Thus, the compounds can be used in therapy against any illness associated with mood swings. The compounds can be used in treatment of the symptoms of mood swings not only seen during hormonal changes in a patient, but also in general, for example where CFR levels are increaseid (e.g. endogenous depression or stress conditions).

The compounds of general formula I can also be used for delaying or preventing loss of cognitive function or enhancing the cognitive function. The compounds can be used in therapy against any illness associated with loss of memory or cognitive performance and in therapy to enhance the cognitive performance. The compounds can be used in treatment of both hormonally related changes and changes of cognitive performance related to normal ageing.

The compounds of the general formula I can furthermore be used in the prevention or treatment of anxiety, depression or sleeplessness.

The present invention is based on the discovery that the compounds of formula I are useful for prevention or treatment of a psychiatric disorder such as mood swings, anxiety, depression or sleeplessness. The present invention furthermore is based on the discovery that the compounds of formula I as stated in claim 1 are useful for delaying or preventing loss of cognitive function or enhancing the cognitive function in a patient.

Within the present invention, compounds of formula I are used for prevention or treatment of one or more psychiatric disorders in a patient.

The term "inhibit" is defined to include its generally accepted meaning which includes prophylactically treating a human subject to incurring the characteristics described, and holding in check and/or treating existing characteristics. As such, the present method includes both medical therapeutic and/or prophylatic treatment, as appropriate. As used herein the term "patient" includes men, women and children.

Psychiatric disorders are those mental disorders which appears in the absence of any known or observable organic/structural brain damage known to be included in the definition by those skilled in the art which includes e.g. anxiety, depression, tension, irritability, memory loss, mood swings, motivational defects, cognitive disorders, attention deficits, schizophrenia, psychoses, winter depressions.

Within formula I, $R^1$, $R^4$ and $R^5$ are individually hydrogen, hydroxy, halogen, trifluoromethyl, $C_{1-6}$ alkyl, $C_{1-6}$ alkoxy or (tertiary amino)($C_{1-6}$ alkoxy); and $R^2$ and $R^3$ are individually hydrogen or a $C_{1-6}$ alkyl. As, used herein, the term "$C_{1-6}$ alkyl" includes straight and branched chain alkyl radicals containing from 1 to 6 carbon atoms, such as methyl, ethyl, n-propyl, isopropyl, n-butyl, tert-butyl, n-amyl, secamyl, n-hexyl, 2-ethylbutyl, 2,3-dimethylbutyl and the like. The term "$C_{1-6}$ alkoxy" includes straight and branched chain alkoxy radicals containing from 1 to 6 carbon atoms, such as methoxy, ethoxy, n-propoxy, isopropoxy, n-butoxy, tert-butoxy, n-amyloxy, sec-amyloxy, n-hexyloxy, 2-ethylbutoxy, 2,3-dimethylbutoxy and the like. "Halogen" includes chloro, fluoro, bromo and iodo. Herein, the term "(tertiary amino)($C_{1-6}$ alkoxy)" is a $C_{1-6}$ alkoxy group which is substituted by a tertiary amino radical. The tertiary amino radical may be a N,N-dialkylamine such as a N,N-dimethylamino, N,N-diethylamino, N,N-dipropylamino and N,N-dibutylamino or a polymethyleneirmine, e.g. piperidine, pyrrolidine, N-methyl-piperazine or morpholine. Preferred compounds include those in which $R^1$ is $C_{1-6}$ alkoxy; $R^2$ and $R^3$ are $C_{1-6}$ alkyl, especially methyl; $R^4$ is hydrogen; and $R^5$ is (tertiary amino)($C_{1-6}$ alkoxy) of the polymethyleneimine type. Within particularly preferred embodiments, $R^1$ is in the 7-position and is $C_{1-6}$ alkoxy, particularly methoxy; each of $R^2$ and $R^3$ is methyl, $R^4$ is hydrogen, and $R^5$ is in the 4-position and is a (tertiary amino)($C_{1-6}$ alkoxy) radical such as 2-(pyrrolidin-1-yl)ethoxy with formula II

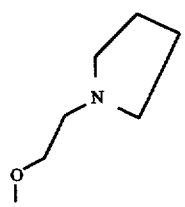

To be included by this invention are all pharmaceutically acceptable salts of the mentioned compounds of formula I.

It is preferred to use the compounds of formula I in the transconfiguration. These compounds may be used as racemic mixtures, or the isolated d- or l- enantiomers may be used. The trans-l-enantiomers are more preferred.

A particularly preferred compound for use within the present invention is centchromran having the formula IV

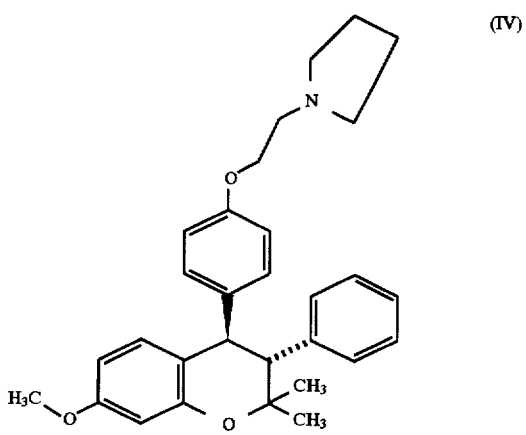

(IV)

Although only one enantiomer is shown, it will be understood that the formula IV is used herein to designate the transconfiguration of the 3- and 4-phenyl groups and that both the d- and l-enantiomers, as well as the racemic mixture, are included.

3,4-diarylchromans are prepared according to known methods, such as those (disclosed in U.S. Pat. No. 3,340,276 to Carney et al., U.S. Pat. No. 3,822,287 to Bolger, and Ray et al., J Med Chem 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer. If $R^2$ is different from R3 and $R^4$ is different from $R^5$, the general formula I covers 8 optical isomers.

Within the present invention, 3,4-diarylchromans of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

3,4-diarylchromans of formula I and their salts are useful within human and veterinary medicine, for example, in the treatment of patients suffering from a psychiatric disorder. For use within the present invention, 3,4-diarylchromans of formula I and their pharmaceutically acceptable salts are formulated with a pharmaceutically acceptable carrier to provide a medicament for parenteral, oral, nasal, rectal, subdermal or intradermal or transdermal administration according to conventional methods. Formmulations may further include one or more diluents, fillers, emulsifiers, preservatives, buffers, excipients, etc, and may be provided in such forms as liquids, powders, emulsions, suppositories, liposomes, transdermal patches, controlled release, dermal implants, tablets, etc. One skilled in this art may formulate the compounds of formula I in an appropriate manner, and in accordance with accepted practices, such as those disclosed in Remington's Pharmaceutical Sciences, Gennaro, ed., Mack Publishing Co., Easton, Pa., 1990.

Oral administration is preferred. Thus, the active compound of formula I is prepared in a form suitable for oral administration, such as a tablet or capsule. Typically, a pharmaceutically acceptable salt of the compound of formula I is combined with a carrier and moulded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions containing a compound of formula I may be administered one or more times per day or week. An effective amount of such a pharmaceutical composition is the amount that provides a clinically significant effect against one or more psychiatric disorders. Such amounts will depend, in part, on the particular condition to be treated, age, weight, and general health of the patient, and other factors evident to those skilled in the art. A typical daily dose will contain a nontoxic dosage range of from about 0.001 to about 75 mg/kg patient per day of a compound of the present invention.

The pharmaceutical compositions containing a compound of formula I may be administered in unit dosage form one or more times per day or week. In the alternative, they may be provided as controlled release formulations suitable for dermal implantation. Implants are formulated to provide release of active compound over the desired period of time, which can he up to several years. Controlled-release formulations are disclosed by, for example, Sanders et al., J Phamr Sci 73 (1964), 1294–1297, 1984; U.S. Pat. No. 4,489,056; and U.S. Pat. No. 4,210,644, which are incorporated herein by reference.

Examples of preferred compounds of formula I are centchroman as a racemic mixture and as isolated l-centchroman and d-centchroman enantiomers. Furthermore, 3,4-trans-2,2-dimethyl-3-phenyl-4-[4-(2-(pyrrolidin-1-yl)ethoxy)phenyl-7-hydroxychroman is a preferred compound. The more preferred compound is isolated l-centchroman (1-3,4-trans-2,2-dimethyl-3-phenyl-4-[4-(2-pyrrolidin-1-yl)ethoxy)phenyl]-7-methoxychroman).

Examples of pharmaceutically acceptable acid addition salts are salts with nontoxic acids, either inorganic acids such as hydrochloric acid, sulphuric acid and phosphoric acid, or organic acids such as formic acid, fumaric acid, acetic acid, propionic acid, succinic acid, gluconic acid, lactic acid, citric acid, ascorbic acid, benzoic acid, embonic acid, methanesulphonic acid and malonic acid.

The present invention is further illustrated by the following examples which, however, are not to be construed as limiting the scope of protection. The features disclosed in the foregoing description and in the following examples may, both separately and in any combination thereof, be material for realising the in- vention in diverse forms thereof.

EXAMPLES

Test 1

Three to fifty women are selected for the clinical study. The women are in general good health, and suffer from one or more of the above-mentioned psychiatric disorders. Because of the idiosyncratic and subjective nature of these disorders, the study has a placebo control group, i.e., the women are divided into two groups, one of which receive the active agent of this invention and the other receive a placebo. Women in the test group receive between 0.001-75 mg/kg patient of the drug per day by the oral route. They continue this therapy for 3-12 months. Accurate records are kept as to the number and severity of the above mentioned disorders in both groups and at the end of the study these results are compared. The results are compared both between members of each group and also the results for each patient are compared to the disorders reported by each patient before the study began.

Utility of the compounds of the invention is illustrated by the positive impact they have on one or more of the psychiatric symptoms/disorders when used in a study as above.

We claim:

1. A method for inhibiting one or more psychiatric disorders in a patient comprising administering to a patient in need thereof a compound of formula I

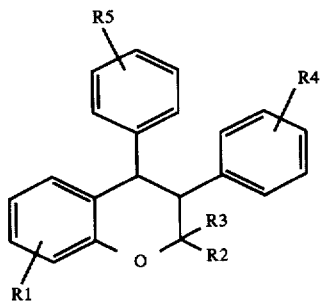

(I)

wherein R1, R4, and R5 are individually hydrogen, hydroxy, halogen, trifluoromethyl, C1–6 alkyl, C1–6 alkoxy or (tertiary amino) (C1–6 alkoxy); and R2 and R3 are individually hydrogen or C1–6 alkyl, or a pharmaceutically acceptable salt thereof in an amount sufficient for said treatment or prophylaxis.

2. The method according to claim 1 wherein the psychiatric disorder is anxiety.

3. The method according to claim 1 wherein the psychiatric disorder is depression.

4. The method according to claim 1 wherein the psychiatric disorder is loss of cognitive function.

5. The method according to claim 1 wherein the psychiatric disorder is mood swings.

6. The method according to claim 1 wherein R1 is C1–6 alkoxy, R2 and R3 are C1–6 alkyl, R4 is hydrogen and R5 is (tertiary amino)(C1–6 alkoxy).

7. The method according to claim 1 wherein R1 is methoxy.

8. The method according to claim 1 wherein R2 is methyl.

9. The method according to claim 1 wherein R3 is methyl.

10. The method according to claim 1 wherein R4 is hydrogen.

11. The method according to claim 1 wherein R5 is a group as stated in formula II below:

(II)

12. The method according to claim 1 wherein said compound is an isolated d- or l-enantiomer.

13. The method according to claim 1 wherein said compound has the general formula III:

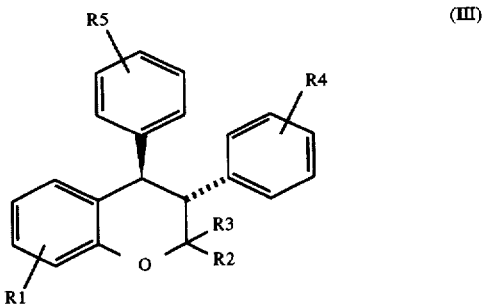

(III)

wherein R1, R4, and R5 are individually hydrogen, hydroxy, halogen, trifluoromethyl, C1–6 alkyl, C1–6 alkoxy or (tertiary amino) (C1–6 alkoxy); and R2 and R3 are individually hydrogen or C1–6 alkyl.

14. The method according to claim 13 wherein said compound is an isolated 1-enantiomer.

15. The method according to claim 1 wherein said compound is centchroman having the formula IV:

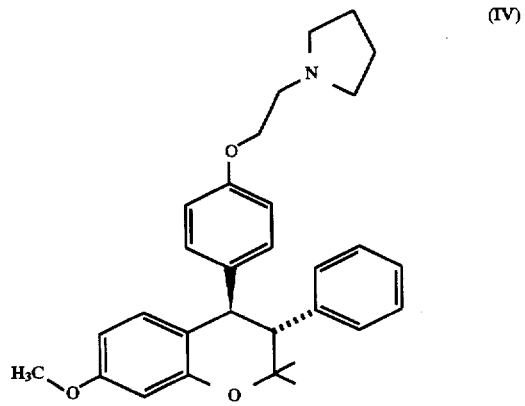

(IV)

16. The method according to claim 15 wherein said compound is an isolated 1-enantiomer.

17. The method according to claim 1 wherein said compound is administered orally.

18. The method according to claim 1 wherein said compound is administered in a range from about 0.001 to 75 mg/kg patient per day.

19. The method according to claim 1 wherein said compound is administered in the form of a dermal implant.

* * * * *